US006951963B2

(12) United States Patent
Lee et al.

(10) Patent No.: US 6,951,963 B2
(45) Date of Patent: Oct. 4, 2005

(54) PROCESS FOR PREPARING N-PROTECTED β-AMINO ALDEHYDE COMPOUNDS

(75) Inventors: Junning Lee, El Granada, CA (US); Jyanwei Liu, Sunnyvale, CA (US)

(73) Assignee: Theravance, Inc., South San Francisco, CA (US)

( * ) Notice: Subject to any disclaimer, the term of this patent is extended or adjusted under 35 U.S.C. 154(b) by 8 days.

(21) Appl. No.: 10/462,150

(22) Filed: Jun. 16, 2003

(65) Prior Publication Data

US 2003/0233010 A1 Dec. 18, 2003

Related U.S. Application Data

(60) Provisional application No. 60/389,261, filed on Jun. 17, 2002.

(51) Int. Cl.$^7$ ............................................. C07D 307/00
(52) U.S. Cl. ...................................... 568/306; 568/307
(58) Field of Search ................................ 568/306, 307; 560/29

(56) References Cited

U.S. PATENT DOCUMENTS 5,594,139 A 1/1997 Varney et al.

FOREIGN PATENT DOCUMENTS

| WO | WO 00/39156 A1 | 7/2000 |
|---|---|---|
| WO | WO 01/57071 A2 | 8/2001 |
| WO | WO 01/98328 A2 | 12/2001 |
| WO | WO 03/018607 A2 | 3/2003 |
| WO | WO 03/029270 A2 | 4/2003 |

OTHER PUBLICATIONS

Liu et. al., "Structure Activity Relationships for Inhibition of Papain by Peptide Michael Acceptors", J. Med. Chem. 1992, 1067–1075.*

Bischofberger, et. al., "Synthesis of Analogues of 1,3–Dihydroxyacetone Phosphate and Glyeraldehyde 3– Phosphate for Use in Studies of Fructose—1,6–diphosphate Aldolase", J. Org. Chem. 1998, 53, 3457–3465.*

Thompson et. al., "Carboxyl–Modified Amino Acids and Pepties as Protease Inhibitors", J. Med. Chem. 1986, 104–111.*

Casreact 113:6779, "Synthesis and inhibiting activity of peptidyl ketones as substrate analogs of papain", European Journal of Medicinal Chemistry (1989), 24(4), 357–62.*

Bischofberger et al., "Synthesis of Analogues of 1,3–Dihydroxyacetone Phosphate and Glyceraldehyde 3–Phosphate for Use in Studies of Fructose–1,6–diphosphate Aldolase", J. Org. Chem., vol. 53, pp 3457–3465 (1988).

Callahan et al., "The Use of γ–Turn Mimetics to Define Peptide Secondary Structure", Tetrahedron, vol. 49, No. 17, pp 3479–3488 (1993).

Giordano et al., "Synthesis and inhibiting activity of peptidylketones as substrate analogues of papain", Eur. J. Med. Chem., vol. 24, pp 357–362 (1989).

Liu et al., "Structure–Activity Relationships for Inhibition of Papain by Peptide Michael Acceptors", J. Med. Chem., vol. 35, pp 1067–1075 (1992).

Thompson et al., "Carboxyl–Modified Amino Acides and Peptides as Protease Inhibitors", J. Med. Chem., vol. 29, pp 104–111 (1986).

Boger et al., "An Improved Syntehsis of 1,2,9,9a– Tetrahydrocyclopropa[c]benz[e]indol–4–one(CBI): A Simplified Analogue of the CC–1065 Alkylation Subunit", J. Org. Chem., 57, pp 2873–2876 (1992).

* cited by examiner

*Primary Examiner*—Cecilia J. Tsang
*Assistant Examiner*—Binta Robinson
(74) *Attorney, Agent, or Firm*—Jeffrey A. Hagenah

(57) ABSTRACT

The invention provides processes for preparing N-protected β-amino aldehyde compounds which are useful as synthetic intermediates for preparing glycopeptide antibiotic derivatives. The processes include cleaving a carbon-carbon double bond to form the N-protected β-amino aldehyde compound.

25 Claims, No Drawings

PROCESS FOR PREPARING N-PROTECTED β-AMINO ALDEHYDE COMPOUNDS

CROSS-REFERENCE TO RELATED APPLICATIONS

This application claims the benefit of U.S. Provisional Application No. 60/389,261, filed on Jun. 17, 2002; the entire disclosure of which is incorporated herein by reference in its entirety.

BACKGROUND OF THE INVENTION

1. Field of the Invention

This invention is directed to novel processes for preparing intermediates which are useful in the synthesis of glycopeptide antibiotic derivatives. More specifically, this invention is directed to processes for preparing β-amino aldehyde compounds in which the amino group is blocked with an amino-protecting group.

2. State of the Art

Glycopeptides (e.g. dalbaheptides) are a well-known class of antibiotics produced by various microorganisms (see *Glycopeptide Antibiotics*, edited by R. Nagarajan, Marcel Dekker, Inc. New York (1994)). These complex peptide compounds are highly effective antibacterial agents useful for treating infections caused by Gram-positive bacteria.

For example, International Publication Numbers WO 00/39156; WO 01/57071 A2; and WO 01/98328 A2 disclose novel glycopeptide derivatives having antibacterial activity. These publications also discloses the use of N-protected β-amino aldehyde compounds, such as N-FMOC-2-(n-decylamino)acetaldehyde, as intermediates in the preparation of such glycopeptide derivatives.

The N-protected β-amino aldehyde compounds disclosed in these publications are prepared in several steps, with the product from each step being isolated separately before the next step. The final step of the disclosed process is an oxidation of the corresponding alcohol using an oxidizing agent, such as sulfur trioxide or oxalyl chloride and dimethyl sulfoxide. Unfortunately, these oxidizing agents produce a unpleasant odor during the reaction process and leave a residue odor in the final product. Accordingly, a need exists for new processes for preparing N-protected β-amino aldehyde compounds.

SUMMARY OF THE INVENTION

The present invention provides an improved process for preparing N-protected β-amino aldehyde compounds, which compounds are useful as intermediates in the preparation of glycopeptide antibiotic derivatives. Among other advantages, the present process provides a high yield of the N-protected β-amino aldehyde compound; can be performed without the need to isolate the reaction intermediates; and does not employ reagents which produce a residual odor in the reaction product.

Accordingly, the present invention provides a process for preparing a N-protected β-amino aldehyde compound of formula I:

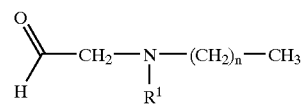

wherein $R^1$ is an amino protecting group; and n is an integer from 7 to 11;

the process comprising cleaving the double bond of a compound of formula II:

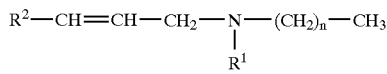

wherein $R^2$ is hydrogen or $C_{1-12}$ hydrocarbyl; to provide a compound of formula I.

In a preferred embodiment, the step of cleaving the double bond is achieved by ozonolysis. Accordingly, in one embodiment, the present invention provides a process for preparing a compound of formula I, the process comprises the steps of:

(a) reacting a compound of formula II with ozone to form an ozonide intermediate; and (b) reacting the ozonide intermediate from step (a) with a reducing agent to form a compound of formula I.

In another preferred embodiment, the step of cleaving the double bond is achieved by reacting a compound of formula II with an oxidizing agent to form a glycol and then oxidizing the glycol with an oxidizing agent.

Accordingly, in another embodiment, the present invention provides a process for preparing a compound of formula I; the process comprising the steps of:

(a) reacting a compound of formula II with a glycol-forming oxidizing agent to form a glycol intermediate; and (b) reacting the glycol intermediate from step (a) with a glycol-cleaving oxidizing agent to form a compound of formula I.

The oxidizing agents employed in steps (a) and (b) of this embodiment may be the same or different; preferably, the oxidizing agents are the same.

Optionally, the above-described processes further comprises the preparation of a compound of formula II before cleaving the carbon-carbon double bond. Accordingly, in another preferred embodiment, the above processes further comprise the steps of:

(a) reacting a compound of formula III:

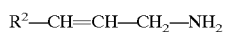

wherein $R^2$ is hydrogen or $C_{1-12}$ hydrocarbyl; with a compound of formula IV:

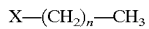

wherein X is a leaving group, and n is an integer from 7 to 11; to provide a compound of formula V:

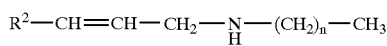

(b) reacting the compound of formula V with an amino-protecting group reagent; to provide a compound of formula II.

In yet another preferred embodiment, the present invention provides a process for preparing a compound of formula Ia:

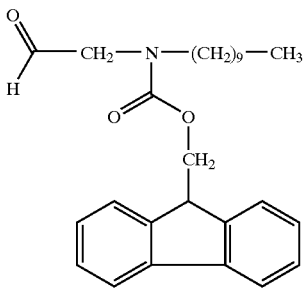

the process comprises the steps of:
(a) reacting allylamine with 1-bromodecane to provide a compound of formula Va:

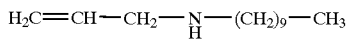

(b) reacting the compound of formula Va with 9-fluorenylmethyl chloroformate; to provide a compound of formula IIa:

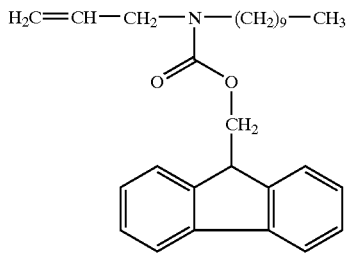

(c) reacting the compound of formula IIa with ozone to form an ozonide intermediate;
(d) reacting the ozonide intermediate from step (c) with a reducing agent to form a compound of formula Ia.

This invention is also directed to the product prepared by any of the processes described herein.

DETAILED DESCRIPTION OF THE INVENTION

The present invention is directed to processes for preparing N-protected β-amino aldehyde compounds, which compounds are useful as intermediates for preparing glycopeptide antibiotic derivatives. When describing the processes and other aspects of the present invention, the following terms have the following meanings unless otherwise indicated.

Definitions

The term "amino-protecting group" refers to a protecting group suitable for preventing undesired reactions at an amino group, and which can be removed by conventional chemical or enzymatic steps to reestablish the amino group. Representative amino-protecting groups include, but are not limited to, include tert-butoxycarbonyl (BOC); trityl (Tr); benzyloxycarbonyl (Cbz); 9-fluorenylmethoxycarbonyl (FMOC); trimethylsilyl (TMS); tert-butyldimethylsilyl (TBS); and the like. Such protecting groups are well-known in the art and are disclosed, for example, in T. W. Greene and P. G. M. Wuts, *Protective Groups in Organic Synthesis*, Third Edition, 1999, John Wiley and Sons, N.Y.

The term "amino-protecting group reagent" refers to a reagent used to protect an amino group. Representative amino-protecting group reagents include, but are not limited to, di-tert-butyl dicarbonate; trityl chloride; benzyl chloroformate; dibenzyl dicarbonate; 9-fluorenylmethyl chloroformate; 9-fluorenylmethoxycarbonyl azide; 1-benzotriazolyl 9-fluorenylmethyl carbonate; 1-succinimidyl 9-fluorenylmethyl carbonate; trimethylsilyl chloride; tert-butyldimethylsilyl chloride; and the like.

The term "hydrocarbyl" refers to an organic radical composed of carbon and hydrogen which may be aliphatic, alicyclic, aromatic or combinations thereof, e.g., aralkyl. Representative hydrocarbyl groups include, but are not limited to, methyl, ethyl, propyl, n-butyl, isobutyl, hexyl, octyl, cyclopentyl, cyclohexyl, phenyl, benzyl, and the like.

The term "glycol" or "glycol intermediate" refers to a vicinal diol. Glycols generally have the formula:

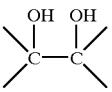

The term "glycopeptide antibiotic" or "glycopeptide" is used herein in its art recognized manner to refer to the class of antibiotics known as glycopeptides or dalbahpeptides. See, for example, R. Nagarajan, "Glycopeptide Anitibiotics", Marcel Dekker, Inc. (1994) and references cited therein. Representative glycopeptides include vancomycin, A82846A (eremomycin), A82846B (chloroorienticin A), A82846C, PA-42867-A (orienticin A), PA-42867-C, PA-42867-D and the like.

The term "leaving group" refers to a functional group or atom which can be displaced by another functional group or atom in a substitution reaction, such as a nucleophilic substitution reaction. By way of example, representative leaving groups include chloro, bromo and iodo groups; and sulfonic ester groups, such as mesylate, tosylate, brosylate, nosylate; and the like.

The terms "ozonide" and "ozonide intermediate" refer to a compound formed when an olefin is treated with ozone, which compound can be reduced to the corresponding aldehydes upon treatment with a reducing agent. Ozonides generally have the formula:

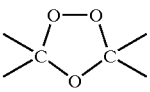

The term "reducing agent" refers to a compound or reagent which is capable of reducing an ozonide to the corresponding aldehyde compounds.

The term "oxidizing agent" refers to a compound or reagent which is either capable of oxidizing an olefin to a glycol (a "glycol-forming oxidizing agent"); or capable of oxidizing a glycol to the corresponding aldehyde compounds (a "glycol-cleaving oxidizing agent").

Preferred Embodiments

Preferably, $R^1$ is an amino-protecting group selected from the group consisting of tert-butoxycarbonyl (BOC); benzyloxycarbonyl (Cbz); and 9-fluorenylmethoxycarbonyl (FMOC). More preferably, $R^1$ is a 9-fluorenylmethoxycarbonyl group.

$R^2$ is preferably hydrogen or $C_{1-12}$ alkyl. More preferably, $R^2$ is hydrogen, methyl or ethyl. Most preferably, $R^2$ is hydrogen.

X is preferably chloro, bromo, iodo, methanesulfonyl or p-toluenesulfonyl. More preferably, X is chloro or bromo. Most preferably, X is bromo.

Preferably, n is an integer from 8 to 10. More preferably, n is 9.

In a particularly preferred embodiment, $R^1$ is a 9-fluorenylmethoxycarbonyl group; $R^2$ is hydrogen; and n is 9 (and when present in the process, X is bromo).

Process Conditions

The processes of the present invention utilize cleavage of a carbon-carbon double bond to generate an aldehyde. The cleavage reaction can be carried out using any suitable reagent which cleaves a carbon-carbon double bond to provide the corresponding aldehydes.

In a preferred embodiment, the cleavage reaction is conducted by contacting a compound of formula II with ozone to form an ozonide intermediate. This ozonide intermediate is typically not isolated, but is reacted in situ with a reducing agent to form an aldehyde of formula I.

The reaction of a compound of formula II with ozone is preferably conducted by contacting the compound of formula II with ozone in an inert diluent. Typically, the ozone is generated from oxygen using any conventional ozone generator and is introduced to the reaction mixture in a stream of oxygen. Ozone is typically introduced into the reaction mixture until essentially all of the compound of formula II has reacted to form an ozonide intermediate.

Preferably, this reaction is conducted at a temperature ranging from about 0° C. to about –65° C.; more preferably, from about –50° C. to about –60° C.; and still more preferably, at about –55° C.

The reaction is preferably conducted in a mixture of dichloromethane and methanol having a v/v ratio of from about 4:1 to about 6:1; more preferably, about 5:1.

The ozonide intermediate formed upon reaction of a compound of formula II with ozone is then reduced with a reducing agent. Any suitable reducing agent can be employed in this reaction.

Preferably, the reducing agent is selected from the group consisting of a trialkylamine; trialkyl phosphite; zinc and acetic acid; catalytic hydrogenation; thiourea; and metal hydrides, such as sodium borohydride, lithium borohydride, zinc borohydride, borane, lithium aluminum hydride and the like.

In a preferred embodiment, the reducing agent is a trialkylamine. More preferably, the reducing agent is trimethylamine or triethylamine; and still more preferably, triethylamine.

Preferably, about 1.0 to about 2.0 molar equivalents of the reducing agent are employed relative to the starting molar equivalents of compound II. More preferably, about 1.1 to about 1.8 molar equivalents are used.

The reducing agent is typically initially contacted with the ozonide intermediate at a temperature ranging from about 0° C. to about –65° C.; more preferably, from about –50° C. to about –60° C.; and still more preferably, at about –55° C. The reaction mixture is then generally allowed to warm to ambient temperature. This reaction is typically conducted for about 1 to about 6 hours; preferably, for about 2 to about 3 hours; or until the reaction is substantially complete.

Alternatively, the cleavage reaction can be conducted by reacting a compound of formula II with a glycol-forming agent to form a glycol intermediate; and then reacting the glycol intermediate with a glycol-cleaving oxidizing agent to form a compound of formula I. The glycol intermediate is typically not isolated, but is reacted in situ with the glycol-cleaving oxidizing agent to form an aldehyde of formula I.

Preferably, the same reagent is used as the glycol-forming oxidizing agent and the glycol-cleaving oxidizing agent. In this embodiment, the oxidizing agent is preferably selected from the group consisting of periodic acid ($HIO_4$); lead tetraacetate ($Pb(OAc)_4$) and sodium periodate ($NaIO_4$). Optionally, a catalytic amount of osmium tetroxide ($OsO_4$) or ruthenium (IV) oxide ($RuO_2$) may be employed in this reaction. Preferred oxidizing agents for this embodiment are sodium periodate with a catalytic amount of osmium tetroxide or ruthenium (IV) oxide.

Generally, this reaction is conducted by contacting the compound of formula II with about 1 to about 10 molar equivalents of the oxidizing agent.

This reaction is typically conducted in an inert diluent at a temperature ranging from about –25° C. to about 50° C. until the cleavage reaction is substantially complete. A suitable inert diluent for sodium periodate/osmium tetroxide is dioxane (and the like); and a suitable inert diluent for lead tetraacetate is toluene (and the like).

In a preferred embodiment, this invention also includes processes for preparing compounds of formula II. In this aspect of the invention, a compound of formula III is first alkylated with a compound of formula IV to provide a compound of formula V.

Representative compounds of formula III suitable for use in this reaction include, but are not limited to, allylamine; 1-aminobut-2-ene(crotyl amine); 1-aminopent-2-ene; 1-aminohex-2-ene; 1-amino-3-phenylprop-2-ene(cinnamyl amine); 1-amino-4-phenylbut-2-ene; and the like. A preferred compound of formula II is allylamine.

Compounds of formula IV suitable for use in this reaction include, but are not limited to, 1-chloroheptane, 1-chlorooctane, 1-chlorononane, 1-chlorodecane, 1-chloroundecane, 1-chlorododecane, 1-bromoheptane, 1-bromooctane, 1-bromononane, 1-bromodecane, 1-bromoundecane, 1-bromododecane, 1-iodoheptane, 1-iodooctane, 1-iodononane, 1-iododecane, 1-iodoundecane, 1-iodododecane, hept-1-yl methanesulfonate, oct-1-yl methanesulfonate, non-1-yl methanesulfonate, dec-1-yl methanesulfonate, undec-1-yl methanesulfonate, dodec-1-yl methanesulfonate, hept-1-yl p-toluenesulfonate, oct-1-yl p-toluenesulfonate, non-1-yl p-toluenesulfonate, dec-1-yl p-toluenesulfonate, undec-1-yl p-toluenesulfonate, dodec-1-yl p-toluenesulfonate. Preferred compounds of formula IV are 1-chlorodecane, 1-bromodecane, dec-1-yl methanesulfonate and dec-1-yl p-toluenesulfonate. A particularly preferred compound of formula IV is 1-bromodecane.

The reaction of a compound of formula III with a compound of formula IV is typically conducted by contacting compound IV with an excess of compound III. Preferably, about 10 to about 50 molar equivalents of compound III are used relative to compound IV; more preferably, about 20 to about 30 molar equivalents. Optionally, this reaction can be conducted in the presence of an inert diluent, but preferably, the reaction is carried out without a diluent.

This reaction is typically conducted at a temperature ranging from about 0° C. to about 50° C., preferably at about 15° C. to about 30° C. for a period ranging from about 2 to about 24 hours, or until the reaction is substantially complete.

When excess allylamine is employed in this reaction, the unreacted allylamine is conveniently removed, and optionally recycled, by distillation following completion of the reaction. Additionally, after removal of the excess allylamine, the reaction mixture is optionally diluted with dichloromethane (or any other suitable diluent) and washed with water and optionally brine. The resulting dichloromethane solution containing a compound of formula V can be used without further isolation of compound V.

The compound of formula V is then reacted with an amino-protecting group reagent to provide a compound of formula II.

Representative amino-protecting group reagents suitable for use in this reaction include, but are not limited to, di-tert-butyl dicarbonate; trityl chloride; benzyl chloroformate; dibenzyl dicarbonate; 9-fluorenylmethyl chloroformate; 9-fluorenylmethoxycarbonyl azide; 1-benzotriazolyl 9-fluorenylmethyl carbonate; 1-succinimidyl 9-fluorenylmethyl carbonate; trimethylsilyl chloride; tert-butyldimethylsilyl chloride; and the like. Preferred amino-protecting group reagents are 9-fluorenylmethyl chloroformate; 9-fluorenylmethoxycarbonyl azide; 1-benzotriazolyl 9-fluorenylmethyl carbonate and 1-succinimidyl 9-fluorenylmethyl carbonate. A particularly preferred amino-protecting group reagent is 9-fluorenylmethyl chloroformate.

This reaction is typically conducted by contacting a compound of formula V with about 0.9 to about 1.1 equivalents of the amino-protecting group reagent in the presence of a trialkylamine or any other suitable base. A preferred trialkylamine is N,N-diisopropylethylamine. Typically, this reaction is conducted in an inert diluent, such as dichloromethane and the like.

Generally, this reaction is conducted at a temperature ranging from about 0° C. to about 30° C., preferably at about 10° C. to about 25° C. for a period ranging from about 1 to about 48 hours, or until the reaction is substantially complete.

In a preferred embodiment, this invention provides a scalable three-step synthesis of N-FMOC-2-(n-decylamino)acetaldehyde from 1-bromodecane without isolating any intermediates. In this embodiment, 1-bromodecane is reacted with excess allylamine in the absence of an inert diluent to afford N-allyldecylamine. Optionally, the excess allylamine is recovered by a simple distillation and can be recycled if desired. Any trace amount of di- and tri-alkylated byproducts form in the reaction can be detected by mass spectrometry and these impurities are easily removed in a dilute acid wash in the work-up following protection of the amino group.

In this procedure, the crude N-allyldecylamine need not be isolated, but is preferably reacted with 9-fluorenylmethyl chloroformate in the presence of N,N-diisopropylethylamine to give N-FMOC-N-allyldecylamine. Surprisingly, use of triethylamine in this reaction gives lower yields. The crude N-FMOC-N-allyldecylamine also need not be isolated and is preferably carried directly into the carbon-carbon double bond cleavage reaction.

When ozone is used to cleave the double bond, triethylamine is preferably used as the reducing agent in the work-up. The resulting triethylamine oxide byproduct is water soluble and is readily removed from the organic layer by an aqueous wash, preferably dilute acid, before final precipitation of N-FMOC-2-(n-decylamino)acetaldehyde.

This three-step process typically gives an overall yield of at least about 61%, based on the 9-fluorenylmethyl chloroformate.

EXAMPLES

The following examples are offered to illustrate this invention and are not to be construed in any way as limiting the scope of this invention. In the examples below, the following abbreviations have the following meanings unless otherwise indicated. Abbreviations not defined below have their generally accepted meaning.

FMOC=9-fluorenylmethoxycarbonyl
HPLC=high performance liquid chromatography
TFA=trifluoroacetic acid All temperatures reported in the following examples are in degrees Celsius (° C.) unless otherwise indicated. Also, unless noted otherwise, reagents, starting materials and solvents were purchased from commercial suppliers (such as Aldrich, Fluka, Sigma and the like) and were used without further purification. Vancomycin hydrochloride semi-hydrate was purchased from Alpharma, Inc., Fort Lee, N.J. 07024 (Alpharma AS, Oslo, Norway).

Unless otherwise indicated, HPLC was conducted under the following conditions:

| Column: | Zorbax BONUS-RP, 5 µm, C18, 4.6 × 150 mm |
|---|---|
| Detector Wavelength: | 254 nm |
| Column Temperature: | 35° C. |
| Flow Rate: | 2 mL/min |
| Solvent System: | A = 98% water, 2% acetonitrile, 1 mL/L TFA |
| | B = 90% acetonitrile, 10% water, 1 mL/L TFA |
| Injection Volume: | 10 µL |
| Run Time: | 10 min |
| Gradient: | 70–100% B in A |

| Time (min) | % A | % B |
|---|---|---|
| 0.0 | 30 | 70 |
| 7.0 | 0 | 100 |
| 9.0 | 0 | 100 |
| 10.0 | 30 | 70 |

| Sample: | Dissolved 20 µL of reaction mixture in 1 mL of B. |
|---|---|

Example 1

Synthesis of N-FMOC-2-(n-Decylamino) acetaldehyde

A three-necked, 1000 mL round bottom flask equipped with a magnetic stir bar and a gas inlet tubing was charged with N-FMOC-N-allyldecylamine (~0.099 mol) in dichloromethane (280 mL) and methanol (50 mL). The mixture was cooled in a −65° C. dry ice-chloroform bath and purged with a stream of dilute ozone in oxygen for 2.5 hours (internal temperature about −55° C.; flow rate for dilute ozone in oxygen about 1.0 L/min). The reaction was monitored by HPLC (retention time for starting material=7.96 min; retention time for product=5.82 min). Upon disappearance of the allyl starting material, ozone purging was discontinued and the mixture was purged with nitrogen for 20 minutes to remove excess ozone. The reaction mixture was then treated with triethylamine (24.8 mL, 0.178 mol) at −55° C., warmed to 21° C., and stirred for 3 hours. The reaction mixture was washed with water (50 mL); 0.01 N HCl (50 mL) and the organic layer was concentrated in vacuo to give an oil. Heptane (150 mL) was added and the mixture was concentrated in vacuo to azeotropically remove water and dichloromethane. This azeotropic procedure was repeated two more times using heptane (150 mL) to give a final volume of about 100 mL. The resulting organic solution was charged to a 200 mL three-necked round bottom flask and cooled to 15° C. in a water bath. Pieces of ice were added slowly to the water bath to cool the mixture to 5° C.

in a period of 40 minutes (the mixture was seeded at approximately 10° C.). The cloudy mixture was further cooled to −10° C. and stirred for 2.5 hours. The resulting suspension was filtered through a Buchner funnel and the precipitate was washed with ice cold heptane (20 mL×2). The precipitate was collected and dried in vacuo (25 mmHg) for 6 hours to give N-FMOC-2-(n-decylamino)acetaldehyde (25.6 g; 61% yield; 99% purity) as a white waxy powder.

The intermediate N-FMOC-N-allyldecylamine was prepared as follows.

a. Synthesis of N-Allyldecylamine.

A three-necked, 500 mL round bottom flask equipped with a thermometer, mechanic stirrer, addition funnel and a distillation apparatus was purged with nitrogen and charged with allylamine (250 mL, 190.25 g, 3.33 mol). 1-Bromodecane (25.0 g, 0.113 mol) was added dropwise over a period of 15 minutes. The reaction was only mildly exothermic (temperature increased from 21° C. to 30° C. in 3 hours). The resulting solution was stirred under nitrogen for 16 hours at 21° C., and the excess allylamine (boiling point 53° C.) was removed by simple distillation in a 90° C. oil bath under nitrogen to give recovered allylamine (210 mL). The milky residue was cooled to 21° C. under nitrogen to give a two-layer mixture (colorless top layer and yellowish bottom layer). Dichloromethane (200 mL) was added to this mixture and the resulting solution was washed with water (100 mL). The organic layer (210 mL) was collected and used in step b below without further purification.

b. Synthesis of N-FMOC-N-Allyldecylamine.

A three-necked, 500 mL round bottom flask equipped with a thermometer, mechanic stirrer and an addition funnel was purged with nitrogen and charged with N-allyldecylamine (~0.11 mol) in dichloromethane from step a (210 mL) and N,N-diisopropylethylamine (20.0 mL, 14.8 g, 0.113 mol). The mixture was cooled in a 5° C. ice bath and a solution of 9-fluorenylmethyl chloroformate (25.6 g, 0.099 mol) dissolved in dichloromethane (50 mL) was added dropwise (total volume approximately 330 mL). The reaction was exothermic and the internal temperature was controlled below 10° C. throughout the 9-fluorenylmethyl chloroformate addition. The reaction mixture was warmed to 21° C. when the addition was finished, and monitored by the disappearance of 9-fluorenylmethyl chloroformate and the formation of N-FMOC-N-allyldecylamine using HPLC (retention time for FMOC-chloride=3.08 min; retention time for product=7.96 min). The reaction mixture was washed with 0.01 N HCl (100 mL). The organic layer was collected and used without further purification.

A representative use of an N-protected β-amino aldehyde compound prepared by the process of this invention is illustrated by the following example.

Example 2

Preparation of N$^{van}$-2-(n-Decylamino)ethyl Vancomycin Hydrochloride

To a stirred mixture of 20 g (13.46 mmol) of vancomycin hydrochloride and 6.526 g (15.48 mmol) of N-Fmoc-2-(n-decylamino)acetyldehyde was added 130 mL of N,N-dimethylformamide and 4.7 mL (26.92 mmol) of N,N-diisopropylethylamine. The resulting mixture was stirred at room temperature under nitrogen for 15 hours, and 75 mL of methanol and 4.15 mL of trifluoroacetic acid (53.84 mmol) were added at 0° C. successively. The mixture was stirred for 1 hour and 1.93 mL (15.48 mmol) of borane-pyridine complex was added. The resulting mixture was stirred for 4 hours at 0° C., and 80 mL (161.52 mmol) of a 2 M methylamine in methanol was added. The resulting mixture was warmed to room temperature and stirred for 50 hours, cooled to 0° C., and water (350 mL) was added dropwise. The mixture was acidified to pH 3.60 by slow addition of 11 mL of concentrated hydrochloric acid, and precipitation occurred. The mixture was stirred for another 30 min and then it was filtered through a Buchner funnel. The resulting wet cake was washed with water (2×200 mL) and dried in vacuo for 16 hours to give 9.8 g of crude N$^{van}$-2-(n-decylamino)ethyl vancomycin hydrochloride.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A process for preparing a compound of formula I:

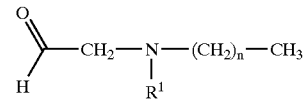

wherein R$^1$ is a 9-fluorenylmethoxycarbonyl group; and n is an integer from 7 to 11;

the process comprising cleaving the double bond of a compound of formula II:

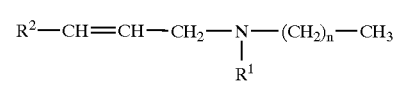

wherein R$^2$ is hydrogen or C$_{1-12}$ hydrocarbyl;

wherein the step of cleaving the double bond comprises the steps of:
(a) reacting a compound of formula II with ozone to form an ozonide intermediate;
(b) reacting the ozonide intermediate from step (a) with a reducing agent to form a compound of formula I;

or the step of cleaving the double bond comprises the steps of:
(a) reacting a compound of formula II with a glycol-forming oxidizing agent to form a glycol intermediate;
(b) reacting the glycol intermediate from step (a) with a glycol-cleaving oxidizing agent to provide a compound of formula I.

2. The process according to claims 1, wherein R$^2$ is hydrogen or C$_{1-12}$ alkyl.

3. The process according to claim 2, wherein R$^2$ is hydrogen.

4. The process according to claim 1, wherein n is an integer from 8 to 10.

5. The process according to claim 4, wherein n is 9.

6. The process according to claim 1, wherein R$^2$ is hydrogen; and n is 9.

7. The process according to claim 1, wherein the step of cleaving the double bond comprises the steps of:
(a) reacting a compound of formula II with ozone to form an ozonide intermediate;
(b) reacting the ozonide intermediate from step (a) with a reducing agent to form a compound of formula I.

8. The process according to claim 7, wherein the reducing agent is a trialkylamine.

9. The process according to claim 8, wherein the reducing agent is triethylamine.

10. The process according to claim 1, wherein the step of cleaving the double bond comprises the steps of:
(a) reacting a compound of formula II with a glycol-forming oxidizing agent to form a glycol intermediate:
(b) reacting the glycol intermediate from step (a) with a glycol-cleaving oxidizing agent to provide a compound of formula I.

11. The process according to claim 10, wherein the oxidizing agent employed in step (a) and step (b) is the same and the oxidizing agent is sodium periodate and catalytic osmium tetroxide or ruthenium (IV) oxide.

12. A process for preparing a compound of formula I:

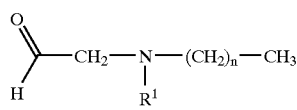

wherein $R^1$ is an amino-protecting group; and n is an integer from 7 to 11;
the process comprising the steps of:
(a) reacting a compound of formula III:

wherein $R^2$ is hydrogen or $C_{1-12}$ hydrocarbyl; with a compound of formula IV:

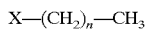

wherein X is a leaving group; to provide a compound of formula V:

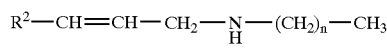

(b) reacting the compound of formula V with an amino-protecting group reagent; to provide a compound of formula II:

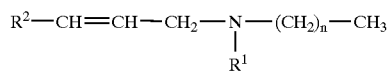

(c) cleaving the double bond of the compound of formula wherein the step of cleaving the double bond comprises the steps of:
(a) reacting a compound of formula II with ozone to form ozonide intermediate;
(b) reacting the ozonide intermediate from step (a) with a reducing agent to form a compound of formula I;
or the step of cleaving the double bond comprises the steps of:
(a) reacting a compound of formula II with a glycol-forming oxidizing agent to form a glycol intermediate:
(b) reacting the glycol intermediate from step (a) with a glycol-cleaving oxidizing agent to provide a compound of formula I.

13. The process according to claim 12, wherein $R^1$ is an amino-protecting group selected from the group consisting of tert-butoxycarbonyl; benzyloxycarbonyl; and 9-fluorenylmethoxycarbonyl.

14. The process according to claim 13, wherein $R^1$ is a 9-fluorenylmethoxycarbonyl group.

15. The process according to claims 12, wherein $R^2$ is hydrogen or $C_{1-12}$ alkyl.

16. The process according to claim 15, wherein $R^2$ is hydrogen.

17. The process according to claim 12, wherein n is an integer from 8 to 10.

18. The process according to claim 17, wherein n is 9.

19. The process according to claim 12, wherein X is chloro or bromo.

20. The process according to claim 19, wherein X is bromo.

21. The process according to claim 1, wherein $R^1$ is a 9-fluorenylmethoxycarbonyl group; $R^2$ is hydrogen; X is bromo; and n is 9.

22. A process for preparing a compound of formula Ia:

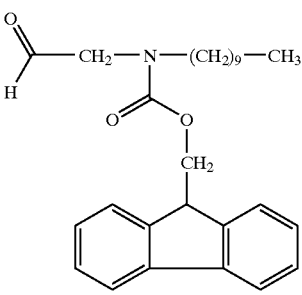

the process comprises the steps of:
(a) reacting allylamine with 1-bromodecane to provide a compound of formula Va:

(b) reacting the compound of formula Va with 9-fluorenylmethyl chloroformate; to provide a compound of formula IIa:

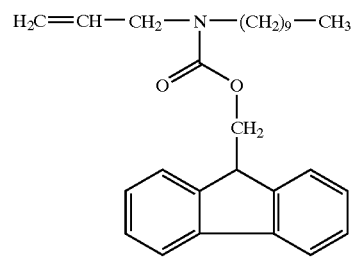

(c) reacting the compound of formula IIa with ozone to form an ozonide intermediate;
(d) reacting the ozonide intermediate from step (c) with a reducing agent to form a compound of formula Ia.

23. The process according to claim 22, wherein the reducing agent is a trialkylamine.

24. The process according to claim 23, wherein the trialkylamine is triethylamine.

25. The product prepared by the process of any of claims 7, 10, 12, or 22.

* * * * *

UNITED STATES PATENT AND TRADEMARK OFFICE
CERTIFICATE OF CORRECTION

PATENT NO. : 6,951,963 B2  Page 1 of 1
APPLICATION NO. : 10/462150
DATED : October 4, 2005
INVENTOR(S) : Junning Lee and Jyanwei Liu It is certified that error appears in the above-identified patent and that said Letters Patent is hereby corrected as shown below:

Column 11,
Line 50, insert -- II -- after "formula";
Line 53, insert -- an -- after "form".

Column 12,
Line 3, "claims" should read -- claim --.

Signed and Sealed this

Twentieth Day of June, 2006

JON W. DUDAS
*Director of the United States Patent and Trademark Office*